US010400125B2

(12) United States Patent
Mori et al.

(10) Patent No.: US 10,400,125 B2
(45) Date of Patent: Sep. 3, 2019

(54) INK COMPOSITION FOR PLASMA TREATMENT DETECTION, AND PLASMA TREATMENT DETECTION INDICATOR

(71) Applicant: SAKURA COLOR PRODUCTS CORPORATION, Osaka-shi, Osaka (JP)

(72) Inventors: Marimo Mori, Osaka (JP); Takeshi Sakumura, Osaka (JP); Yasuaki Hirata, Osaka (JP)

(73) Assignee: SAKURA COLOR PRODUCTS CORPORATION, Osaka-shi (JP)

(*) Notice: Subject to any disclaimer, the term of this patent is extended or adjusted under 35 U.S.C. 154(b) by 0 days.

(21) Appl. No.: 15/316,980

(22) PCT Filed: Aug. 25, 2015

(86) PCT No.: PCT/JP2015/073769
§ 371 (c)(1),
(2) Date: Dec. 7, 2016

(87) PCT Pub. No.: WO2016/042980
PCT Pub. Date: Mar. 24, 2016

(65) Prior Publication Data
US 2017/0101548 A1 Apr. 13, 2017

(30) Foreign Application Priority Data

Sep. 16, 2014 (JP) ................. 2014-187548
May 7, 2015 (JP) ................. 2015-095244

(51) Int. Cl.
C09D 11/50 (2014.01)
C09D 11/03 (2014.01)
C09D 11/033 (2014.01)
C09D 11/037 (2014.01)
C09D 11/102 (2014.01)
C09D 11/106 (2014.01)
B65D 25/54 (2006.01)
B65D 5/42 (2006.01)
B65D 75/52 (2006.01)
B65D 81/20 (2006.01)
B08B 7/00 (2006.01)
H01J 37/32 (2006.01)
A61L 2/14 (2006.01)
A61L 2/28 (2006.01)
C09D 11/14 (2006.01)

(52) U.S. Cl.
CPC .............. C09D 11/50 (2013.01); A61L 2/14 (2013.01); A61L 2/28 (2013.01); B08B 7/0035 (2013.01); B65D 25/54 (2013.01); B65D 81/20 (2013.01); C09D 11/03 (2013.01); C09D 11/037 (2013.01); C09D 11/106 (2013.01); C09D 11/14 (2013.01); H01J 37/3244 (2013.01)

(58) Field of Classification Search
CPC ....... C09D 11/50; C09D 11/03; C09D 11/033; C09D 11/037; C09D 11/102; C09D 11/106; C09D 11/14; A61L 2/114; A61L 2/28; B65D 5/4216; B65D 25/54; B65D 75/522; B65D 81/2084; H01J 37/32963; H01J 37/32972; B08B 7/0035
USPC .................. 106/31.32, 31.64; 436/1; 422/28
See application file for complete search history.

(56) References Cited

U.S. PATENT DOCUMENTS

| 4,155,895 | A | 5/1979 | Rohowetz et al. |
| 4,179,397 | A | 12/1979 | Rohowetz et al. |
| 4,839,311 | A | 6/1989 | Riley et al. |
| 5,955,025 | A | 9/1999 | Barrett |
| 5,990,199 | A | 11/1999 | Bealing et al. |
| 6,063,631 | A | 5/2000 | Ignacio |
| 6,117,685 | A | 9/2000 | Omatsu et al. |
| 6,267,242 | B1* | 7/2001 | Nagata ............ A61L 2/28 422/28 |
| 6,355,448 | B1 | 3/2002 | Foltz et al. |
| 6,410,338 | B1 | 6/2002 | Lippold et al. |
| 6,524,763 | B1 | 2/2003 | Kuroda et al. |
| 6,852,281 | B2 | 2/2005 | Inoue et al. |

(Continued)

FOREIGN PATENT DOCUMENTS

| CN | 1777644 A | 5/2006 |
| CN | 1877777 A | 12/2006 |

(Continued)

OTHER PUBLICATIONS

English translation of the Written Opinion of the International Search Authority dated Nov. 17, 2015 for PCT/JP2015/073769; 4 pages.*
English translation of JP 2013/233387, Nov. 2013; 9 pages.*
English translation of JP 2004/298479, Oct. 2004; 12 pages.*
English translation of JP 2013/095764, May 2013; 14 pages.*
English translation of JP 2013/095765, May 2013; 14 pages.*
English translation of JP 2013/098196, May 2013; 11 pages.*
Nagatsu, Plasma Sterilization, Journal of Plasma and Fusion Research vol. 83, No. 7 (2007), with English abstract (7 pages).

(Continued)

Primary Examiner — Helene Klemanski
(74) Attorney, Agent, or Firm — Westerman, Hattori, Daniels & Adrian, LLP

(57) ABSTRACT

Provided is a plasma treatment detection indicator that enables the completion of plasma treatment to be confirmed from the color change of a color-changing layer by controlling the color change rate, regardless of whether the type of plasma is reduced-pressure plasma or atmospheric-pressure plasma, and regardless of the degree of plasma intensity; also provided is an ink composition for detecting plasma treatment for forming the color-changing layer.
The ink composition for detecting plasma treatment comprises an organic dye and at least one member selected from the group consisting of a photopolymerization initiator, silica, and hydrophobic alumina.

10 Claims, No Drawings

(56) References Cited

U.S. PATENT DOCUMENTS

| | | | |
|---|---|---|---|
| 7,189,355 B2 | 3/2007 | Mikumo et al. | |
| 7,364,700 B2 | 4/2008 | Maruo et al. | |
| 7,364,770 B2 | 4/2008 | Nagashima et al. | |
| 7,678,858 B2 | 3/2010 | Tanaka et al. | |
| 7,976,781 B2 | 7/2011 | Maruo et al. | |
| 7,981,687 B2 | 7/2011 | Yamaguchi et al. | |
| 8,222,327 B2 | 7/2012 | Mikumo et al. | |
| 8,530,242 B2 | 9/2013 | Lin et al. | |
| 2001/0054374 A1 | 12/2001 | Omatsu et al. | |
| 2002/0051733 A1 | 5/2002 | Antonoplos et al. | |
| 2002/0121629 A1 | 9/2002 | Mikumo et al. | |
| 2005/0054374 A1 | 3/2005 | Namiki | |
| 2006/0194056 A1 | 8/2006 | Nagashima et al. | |
| 2006/0235140 A1 | 10/2006 | Tanaka et al. | |
| 2006/0244379 A1 | 11/2006 | Shin | |
| 2006/0283746 A1* | 12/2006 | Sutoh | A61L 2/28 206/439 |
| 2008/0090726 A1 | 4/2008 | Eskra et al. | |
| 2008/0157486 A1 | 7/2008 | Kuzawa et al. | |
| 2008/0267811 A1* | 10/2008 | Yamaguchi | G01N 31/223 106/31.32 |
| 2009/0212237 A1 | 8/2009 | Sugiki et al. | |
| 2010/0119410 A1* | 5/2010 | Yamaguchi | A61L 2/14 422/23 |
| 2011/0009535 A1 | 1/2011 | Mikumo et al. | |
| 2011/0065203 A1* | 3/2011 | Studer | C09D 11/50 436/164 |
| 2011/0275159 A1 | 11/2011 | Landgrebe et al. | |
| 2011/0312096 A1 | 12/2011 | Whitman et al. | |
| 2012/0100395 A1* | 4/2012 | Feiler | C09D 11/50 428/704 |
| 2012/0149037 A1 | 6/2012 | Bommarito et al. | |
| 2012/0315659 A1 | 12/2012 | Andreescu et al. | |
| 2014/0154808 A1 | 6/2014 | Patel | |
| 2014/0216636 A1 | 8/2014 | Kuzawa et al. | |
| 2015/0050745 A1 | 2/2015 | Karato et al. | |
| 2016/0045631 A1* | 2/2016 | Yamaguchi | A61L 2/14 422/28 |
| 2016/0133444 A1* | 5/2016 | Oshiro | C09D 11/033 216/60 |
| 2016/0141192 A1* | 5/2016 | Uneyama | C09D 11/50 116/201 |
| 2016/0349222 A1* | 12/2016 | Mori | H01J 37/32917 |
| 2016/0349224 A1 | 12/2016 | Patel et al. | |
| 2017/0044389 A1* | 2/2017 | Mori | H01L 21/3065 |
| 2017/0101548 A1 | 4/2017 | Mori et al. | |
| 2017/0153174 A1 | 6/2017 | Yamakawa et al. | |
| 2017/0261476 A1 | 9/2017 | Hishikawa et al. | |
| 2017/0330777 A1 | 11/2017 | Hishikawa et al. | |

FOREIGN PATENT DOCUMENTS

| | | | |
|---|---|---|---|
| CN | 101014668 A | 8/2007 | |
| CN | 101230247 A | 7/2008 | |
| EP | 1312918 A2 | 5/2003 | |
| GB | 2 168 082 A | 6/1986 | |
| JP | 54-088068 A | 7/1979 | |
| JP | S63-36876 | 2/1988 | |
| JP | 1-295423 A | 11/1989 | |
| JP | 4-305492 A | 10/1992 | |
| JP | 3-69165 A | 3/1994 | |
| JP | 7-26477 A | 1/1995 | |
| JP | 11-37988 A | 2/1999 | |
| JP | 2000-269191 A | 9/2000 | |
| JP | 2001-174449 A | 6/2001 | |
| JP | 2001-237097 A | 8/2001 | |
| JP | 2001-242249 A | 9/2001 | |
| JP | 2002-011081 A | 1/2002 | |
| JP | 2002-22534 A | 1/2002 | |
| JP | 2002-502953 A | 1/2002 | |
| JP | 2002-303618 A | 10/2002 | |
| JP | 2002/322315 A | 11/2002 | |
| JP | 2002-323451 A | 11/2002 | |
| JP | 2003-506156 A | 2/2003 | |
| JP | 2003-119087 A | 4/2003 | |
| JP | 2003-515744 A | 5/2003 | |
| JP | 2003-325646 A | 11/2003 | |
| JP | 2004-101488 A | 4/2004 | |
| JP | 2004-146738 A | 5/2004 | |
| JP | 2004-146739 A | 5/2004 | |
| JP | 2004-203984 A | 7/2004 | |
| JP | 2004/298479 | * 10/2004 | |
| JP | 2005-111154 A | 4/2005 | |
| JP | 2005-142287 A | 6/2005 | |
| JP | 2005-315828 A | 11/2005 | |
| JP | 2005-329019 A | 12/2005 | |
| JP | 2006-78463 A | 3/2006 | |
| JP | 2006-223351 A | 8/2006 | |
| JP | 2007-040785 A | 2/2007 | |
| JP | 2008-125760 A | 6/2008 | |
| JP | 2009-213609 A | 9/2009 | |
| JP | 2010-501655 A | 1/2010 | |
| JP | 2011-530085 A | 12/2011 | |
| JP | 2012-050664 A | 3/2012 | |
| JP | 2012-068811 A | 4/2012 | |
| JP | 2012-78202 A | 4/2012 | |
| JP | 2013-95764 A | 5/2013 | |
| JP | 2013-095765 A | 5/2013 | |
| JP | 2013-95765 A | 5/2013 | |
| JP | 2013-98196 A | 5/2013 | |
| JP | 2013/233387 | * 11/2013 | |
| JP | 2014-109523 A | 6/2014 | |
| JP | 2016-111063 A | 6/2016 | |
| WO | 98/46279 A1 | 10/1998 | |
| WO | 98/46994 A1 | 10/1998 | |
| WO | 99/39754 A1 | 8/1999 | |
| WO | 01/10476 A1 | 2/2001 | |
| WO | 01/40792 A1 | 6/2001 | |
| WO | 2004/087222 A1 | 10/2004 | |
| WO | 2006/109726 A1 | 10/2006 | |
| WO | 2008/022952 A1 | 2/2008 | |
| WO | 2009/128988 A1 | 10/2009 | |
| WO | 2013/129473 A1 | 9/2013 | |
| WO | 2014/038612 A1 | 3/2014 | |
| WO | WO 2014/196440 A1 * | 12/2014 | |
| WO | WO 2015/025699 A1 * | 2/2015 | |
| WO | 2015/170592 A1 | 11/2015 | |

OTHER PUBLICATIONS

International Search Report dated Nov. 17, 2015, issued in counterpart International Application No. PCT/JP2015/073769 (1 page).

International Search Report dated Jul. 14, 2015, issued in counterpart International Application No. PCT/JP2015/061545; 4 pages.

International Search Report dated Sep. 2, 2014, issued in counterpart Application No. PCT/JP2014/064209; 2 pages.

Non-Final Office Action dated Jun. 28, 2017; issued in U.S Appl. No. 14/895,835; 19 pages.

Non-Final Office Action dated Jul. 3, 2017; Issued in U.S. Appl. No. 15/305,822; 142 pages.

Final Office Action dated Nov. 17, 2017, issued in U.S. Appl. No. 14/895,835. (18 pages).

International Search Report dated Apr. 14, 2015, issued in International Application No. PCT/JP2015/053742 (1 page).

International Search Report dated Feb. 9, 2016, issued in Application No. PCT/JP2015/082841 (2 pages).

International Search Report dated Sep. 16, 2014, issued in Application No. PCT/JP2014/070419 (2 pages).

Office Action dated Mar. 14, 2017, issued in Chinese Application No. 201480033301.2, with partial English translation (11 pages).

Office Action dated Jun. 9, 2010, issued in counterpart Japanese Application No. 2005-064179 (2 pages).

International Search Report dated May 17, 2005, issued in Application No. PCT/JP2005/006138 (1 page).

Non-Final Office Action dated Mar. 4, 2009, issued in U.S. Appl. No. 10/594,587 (9 pages).

Final Office Action dated Nov. 27, 2009, issued in U.S. Appl. No. 10/594,587 (11 pages).

Non-Final OA dated Jun. 11, 2010, issued in U.S. Appl. No. 10/594,587 (6 pages).

(56) References Cited

OTHER PUBLICATIONS

Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Non-Final Office Action dated Dec. 19, 2017, issued in U.S. Appl. No. 15/309,510 (16 pages).
Non-Final Office Action dated Jan. 31, 2018, issued in U.S. Appl. No. 15/529,382 (25 pages).
Non-Final Office Action dated Nov. 20, 2017, issued in U.S. Appl. No. 14/897,461 (27 pages).
International Search Report dated Jul. 14, 2015 issued in International Application No. PCT/JP2015/062244 (2 pages).
Non-Final Office Action dated Mar. 1, 2018, issued in U.S. Appl. No. 15/305,822, (7 pp).
English Translation of JP2002/303618, Oct. 2002; (14 pp) cited in Non-Final Office Action dated Mar. 1, 2018 for U.S. Appl. No. 15/305,822.
English Translation of JP 2004/101488, Apr. 2004 (9 pp) cited in Non-Final Office Action dated Mar. 1, 2018 for U.S. Appl. No. 15/305,822.
English Translation of WO 2014/038612, Mar. 2014 (10 pp) cited in Non-Final Office Action dated Mar. 1, 2018 for U.S. Appl. No. 15/305,822.
Janus Green B, no date available; https://pubchem.ncbi.nlm.nih.gov/compound/Janus_green_B (17 pp) cited in Non-Final Office Action dated Mar. 1, 2018 for U.S. Appl. No. 15/305,822.
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp (3 pp) cited in Non-Final Office Action dated Mar. 1, 2018 for U.S. Appl. No. 15/305,822.
Sylowhite SM 405, Jul. 2009, http://novana.ch/news/8/3/0/sylowhite-sm-405 (1 page) cited in Non-Final Office Action dated Mar. 1, 2018 for U.S. Appl. No. 15/305,822.
Final Office Action dated Nov. 17, 2017, issued in U.S. Appl. No. 15/305,822, (13 pages).
Office Action dated Mar. 20, 2018, issued in counterpart Japanese Application No. 2014-087638, with English translation (9 pages).
Notice of Allowance dated May 1, 2018, issued in U.S. Appl. No. 14/897,461 (27 pages).
Notice of Allowance dated Apr. 27, 2018, issued in U.S. Appl. No. 15/309,510 (24 pages).
International Search Report dated Mar. 1, 2016, issued in counterpart International Application No. PCT/JP2015/082818 (2 pages).
Office Action dated Sep. 28, 2010, issued in counterpart Japanese Application No. 2005-064179, with English translation (5 pages).
Office Action dated Mar. 26, 2013, issued in counterpart Japanese Application No. 2010-263654, with English translation (5 pages).
Notice of Allowance dated May 17, 2018, issued in U.S. Appl. No. 15/117,601 (28 pages).
Non-Final Office Action dated May 17, 2018, issued in U.S. Appl. No. 15/117,601 (28 pages).
Final Office Action dated May 25, 2018, issued in U.S. Appl. No. 15/529,382 (37 pages).
Notice of Allowance dated Aug. 15, 2018, issued in U.S. Appl. No. 15/529,382 (16 pages).
Notice of Allowance dated Aug. 7, 2018, issued in U.S. Appl. No. 15/305,822 (18 pages).
Kitaoka, Kyozo, "Guide for Coatings to Synthetic Resin", May 25, 1974, First Edition, pp. 212-213, with English translation; Cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation; Cited in Japanese Office Action dated Aug. 21, 2018.
Office Action dated Aug. 21, 2018, issued in Japanese Application No. 2014-087638, with English translation (7 pages).
Notice of Allowance dated Sep. 6, 2018, issued in U.S. Appl. No. 15/309,510 (13 pages).
Final Office Action dated Sep. 20, 2018, issued in U.S. Appl. No. 15/117,601 (21 pages).
Office Action having a Date of Drafting of Aug. 22, 2018, issued in counterpart Japanese Application No. 2015-532792, with English translation (6 pages).
Office Action dated Sep. 5, 2018 issued in Chinese application No. 201580020478.3, with English translation. (12 pages).
Office Action dated Oct. 9, 2018, issued in Japanese Application No. 2015-562838, with English translation (5 pages).
Office Action dated Oct. 9, 2018, issued in Japanese Application No. 2014-244414, with English translation (7 pages).
Final Office Action dated Oct. 29, 2018, issued in U.S. Appl. No. 15/117,601, (15 pages).
Office Action dated Dec. 4, 2018, issued in counterpart Japanese Application No. 2015-095244, with English translation (5 pages).
Office Action dated Dec. 25, 2018, issued in counterpart CN Application No. 201580007914.3, with English translation (15 pages).
Office Action dated Feb. 5, 2019, issued in counterpart JP Application No. 2015-532792, with English translation (9 pages).
Notice of Allowance dated Apr. 22, 2019, issued in U.S. Appl. No. 15/117,601 (9 pages).

* cited by examiner

INK COMPOSITION FOR PLASMA TREATMENT DETECTION, AND PLASMA TREATMENT DETECTION INDICATOR

TECHNICAL FIELD

The present invention relates to an ink composition for detecting plasma treatment and to a plasma treatment detection indicator using the composition. The plasma treatment as referred to here means a plasma treatment using plasma generated by applying AC voltage, pulse voltage, high-frequency waves, microwaves, etc., using a gas for generating plasma. The plasma treatment includes both reduced-pressure plasma and atmospheric-pressure plasma.

BACKGROUND ART

Various types of equipment, instruments, etc., used in hospitals, laboratories, and the like are sterilized for disinfection and killing bacteria and fungi. Plasma treatment is known as a sterilization treatment (see, for example, "3.3.1 Sterilization Experiment Using Low-pressure Discharge Plasma" in Non-patent Literature 1).

Plasma treatment is used not only for sterilization treatment but also for plasma dry-etching and plasma cleaning of the surface of articles to be treated, such as electronic parts, in the production of semiconductor devices.

Plasma dry-etching generally comprises applying high-frequency power to electrodes placed in a reaction chamber that is a vacuum vessel, plasmarizing a gas for generating plasma introduced in the reaction chamber, and etching a semiconductor wafer with high precision. Plasma cleaning removes metal oxides, organic substances, burrs, etc., deposited on or adhering to the surface of articles to be treated, such as electronic parts, to improve bonding or wettability of solder, thus enhancing bonding strength and improving adhesion to a sealing resin and wettability.

A method using a plasma treatment detection indicator comprising a color-changing layer that changes color in a plasma treatment atmosphere is known as a method for detecting the completion of these plasma treatments.

For example, Patent Literature 1 discloses an ink composition for detecting plasma treatment, the composition comprising 1) at least one of anthraquinone colorants, azo colorants, and phthalocyanine colorants, and 2) at least one of binder resins, cationic surfactants, and extenders, wherein a gas for generating plasma used in the plasma treatment contains at least one of oxygen and nitrogen; Patent Literature 1 also discloses a plasma treatment detection indicator comprising a color-changing layer formed from the ink composition formed on a base material.

Patent Literature 2 discloses an ink composition for detecting inert gas plasma treatment, the composition comprising 1) at least one of anthraquinone colorants, azo colorants, and methine colorants, and 2) at least one of binder resins, cationic surfactants, and extenders, the inert gas containing at least one selected from the group consisting of helium, neon, argon, krypton, and xenon; Patent Literature 2 also discloses a plasma treatment detection indicator comprising a color-changing layer formed from the ink composition formed on a base material.

These plasma treatment detection indicators are useful indicators that allow the completion of plasma treatment to be determined from the color change of the color-changing layer.

However, there are indications that with these plasma treatment detection indicators, the color change of the color-changing layer may be slow and the completion of plasma treatment may not be determined accurately, especially when the plasma intensity is set to be low in reduced-pressure plasma or when atmospheric-pressure plasma, which generally has plasma intensity lower than that of reduced-pressure plasma, is used. Accordingly, there is room for improvement in color change properties.

Thus, in view of the problems described above, there is demand for the development of a plasma treatment detection indicator that enables the completion of plasma treatment to be confirmed from the color change of a color-changing layer by controlling the color change rate, regardless of whether the type of plasma is reduced-pressure plasma or atmospheric-pressure plasma, and regardless of the degree of plasma intensity; also demanded is an ink composition for detecting plasma treatment for forming the color-changing layer.

CITATION LIST

Patent Literature

PTL 1: JP2013-098196A
PTL 2: JP2013-095764A

Non-Patent Literature

NPL 1: Journal of Plasma and Fusion Research Vol. 83, No. 7 July 2007

SUMMARY OF INVENTION

Technical Problem

An object of the present invention is to provide a plasma treatment detection indicator that enables the completion of plasma treatment to be confirmed from the color change of a color-changing layer by controlling the color change rate, regardless of whether the type of plasma is reduced-pressure plasma or atmospheric-pressure plasma, and regardless of the degree of plasma intensity; and is also to provide an ink composition for detecting plasma treatment for forming the color-changing layer.

Solution to Problem

The present inventors conducted extensive research to achieve the above object and found that the object can be achieved by using an ink composition of a specific formulation. The present invention has thus been accomplished.

Specifically, the present invention relates to the following ink composition for detecting plasma treatment and plasma treatment detection indicator.

1. An ink composition for detecting plasma treatment, the composition comprising an organic dye and at least one member selected from the group consisting of a photopolymerization initiator, silica, and hydrophobic alumina.
2. The ink composition according to Item 1, further comprising a cellulose resin.
3. The ink composition according to Item 1, further comprising a polyvinyl butyral resin.
4. The ink composition according to any one of Items 1 to 3, wherein the organic dye is at least one member selected from the group consisting of nitroso dyes, nitro dyes, monoazo dyes, diazo dyes, triazo dyes, polyazo dyes, azoic dyes (diazo components), azoic dyes (coupling components), stilbene dyes, carotenoid dyes, diarylmethane dyes, triarylmethane dyes, xanthene dyes, acridine dyes, quinoline dyes, methine dyes, thiazole dyes, indamine dyes, indophenol dyes, azine dyes, oxazine dyes, thiazin dyes, sulfur dyes, lactone dyes, hydroxyketone dyes, aminoketone dyes, anthraquinone dyes, indigoid dyes, phthalocyanine dyes, natural dyes, and oxidation dyes.

5. The ink composition according to any one of Items 1 to 4, wherein the photopolymerization initiator is at least one member selected from the group consisting of alkylphenone-based photopolymerization initiators, acylphosphine oxide-based photopolymerization initiators, titanocene-based photopolymerization initiators, acetophenone-based photopolymerization initiators, benzophenone-based photopolymerization initiators, thioxanthone-based photopolymerization initiators, cationic photopolymerization initiators, and anionic photopolymerization initiators.

6. The ink composition according to any one of Items 1 to 5, further comprising an extender.

7. A plasma treatment detection indicator comprising a color-changing layer formed from the ink composition according to any one of Items 1 to 6.

8. A plasma treatment package comprising a gas-permeable package and the indicator according to Item 7 in the gas-permeable package.

9. The package according to item 8, having a transparent window in a part of the package so as to enable the indicator to be checked from the outside.

10. A plasma treatment method comprising placing an article to be treated in the package according to Item 8 or 9, sealing the package containing the article to be treated, and placing the package in a plasma treatment atmosphere.

11. The treatment method according to Item 10, wherein the package is placed in the plasma treatment atmosphere until the color-changing layer of the indicator changes color.

Advantageous Effects of Invention

Since the ink composition for detecting plasma treatment of the present invention contains an organic dye as a color-changing component that changes color in a plasma treatment atmosphere, and further contains at least one member selected from the group consisting of photopolymerization initiators, silica, and hydrophobic alumina, a color-changing layer formed from the ink composition exhibits more excellent color change properties (color change rate) than conventional products in a plasma treatment atmosphere.

Thus, regardless of whether the type of plasma is reduced-pressure plasma or atmospheric-pressure plasma, and regardless of the degree of plasma intensity, a plasma treatment detection indicator comprising the color-changing layer allows the completion of plasma treatment to be precisely confirmed from the color change of the color-changing layer by controlling the color change rate.

DESCRIPTION OF EMBODIMENTS

The ink composition for detecting plasma treatment and the plasma treatment detection indicator of the present invention are described below in detail.

1. Ink Composition for Detecting Plasma Treatment

The ink composition for detecting plasma treatment of the present invention ("ink composition") contains an organic dye and at least one member selected from the group consisting of photopolymerization initiators, silica, and hydrophobic alumina.

Since the ink composition for detecting plasma treatment of the present invention, which has the above feature, contains an organic dye as a color-changing component that changes color in a plasma treatment atmosphere and further contains at least one member selected from the group consisting of photopolymerization initiators, silica, and hydrophobic alumina, a color-changing layer formed from the ink composition exhibits more excellent color change properties (color change rate) than conventional products in a plasma treatment atmosphere. Thus, regardless of whether the type of plasma is reduced-pressure plasma or atmospheric-pressure plasma, and regardless of the degree of plasma intensity, a plasma treatment detection indicator comprising the color-changing layer allow the completion of plasma treatment to be precisely confirmed from the color change of the color-changing layer by controlling the color change rate.

The following describes each component of the ink composition.

Color-Changing Component in Plasma Treatment Atmosphere

The ink composition of the present invention contains an organic dye as a color-changing component for detecting plasma in a plasma treatment atmosphere. The organic dye exhibits color change behavior due to change in its structure (such as partial decomposition or bond cleavage) caused by the action of plasma in a plasma treatment atmosphere. The organic dye generally changes from colored to colorless due to the action of plasma.

The organic dye may be any organic dye that exhibits the behavior described above. For example, the organic dye can be suitably selected from the group consisting of direct dyes, acid dyes, basic dyes, mordant dyes, vat dyes, disperse dyes, reactive dyes, and fluorescent whitening dyes. More specifically, the organic dye is, for example, at least one member selected from the group consisting of nitroso dyes (10000-10299), nitro dyes (10300-10999), monoazo dyes (11000-19999), diazo dyes (20000-29999), triazo dyes (30000-34999), polyazo dyes (35000-36999), azoic dyes (diazo components) (37000-37275), azoic dyes (coupling components) (37500-37625), stilbene dyes (40000-40799), carotenoid dyes (40800-40999), diarylmethane dyes (41000-41999), triarylmethane dyes (42000-44999), xanthene dyes (45000-45999), acridine dyes (46000-46999), quinoline dyes (47000-47999), methine dyes (48000-48999), thiazole dyes (49000-49399), indamine dyes (49400-49699), indophenol dyes (49700-49999), azine dyes (50000-50999), oxazine dyes (51000-51999), thiazine dyes (52000-52999), sulfur dyes (53000-53999), lactone dyes (54000-54999), hydroxyketone dyes (55000-55999), aminoketone dyes (56000-56999), anthraquinone dyes (58000-72999), indigoid dyes (73000-73999), phthalocyanine dyes (74000-74999), natural dyes (75000-75999), and oxidation dyes (76000-76999) (color index (CI) numbers are in parentheses). Among the organic dyes above, at least one member selected from the group consisting of the anthraquinone dyes and triarylmethane dyes described below is preferable.

Anthraquinone dyes may be any dye that has anthraquinone as a basic skeleton. Anthraquinone disperse dyes and the like are also usable. In particular, anthraquinone dyes containing an amino group are preferable. Anthraquinone dyes containing at least one amino group selected from primary amino groups and secondary amino groups are more preferable. In this case, two or more amino groups may be present, and these amino groups may be of the same or different type.

Specific examples include 1,4-diaminoanthraquinone (C.I. Disperse Violet 1), 1-amino-4-hydroxy-2-methylaminoanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraaminoanthraquinone (C.I. Disperse Blue 1), 1,4-diamino-5-nitroanthraquinone (C.I. Disperse Violet 8), and the like (color index names are in parentheses).

Other usable dyes include those known as C.I. Solvent Blue 14, C.I. Solvent Blue 35, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19, C.I. Disperse Blue 7, and the like. Among these anthraquinone dyes, C.I. Disperse Blue 7, C.I. Disperse Violet 1, and the like are preferable.

Triarylmethane dyes may be any dye that has a triarylmethane structure. Examples include C.I. Acid Blue 90, C.I. Acid Green 16, C.I. Acid Violet 49, C.I. Basic Red 9, C.I. Basic Blue 7, C.I. Acid Violet 1, C.I. Direct Blue 41, C.I. Mordant Blue 1, C.I. Mordant Violet 1, and the like.

These organic dyes can be used singly or in a combination of two or more. The color (the type or density of color) in a color change state and detection sensitivity can be freely adjusted by changing the type of dye or the mixing combination.

The content of the organic dye can be appropriately determined according to, for example, the type of organic dye and the desired hue. The ink composition generally preferably contains an organic dye in an amount of about 0.05 to 20 wt. %, particularly preferably 0.1 to 10 wt. An organic dye content exceeding 20 wt. % may reduce solubility or dispersibility in a solvent during preparation of the ink composition or may make it difficult to form a uniform coating film of the ink composition during formation of a color-changing layer. In addition, when an indicator is prepared, the color (color before color change) of the color-changing layer may be too dark. On the other hand, if the content of the organic dye is less than 0.05 wt. %, when an indicator is prepared, the color (color before color change) of the color-changing layer may be too light, and, in particular, gradation may decrease because of less change in hue along with change in the thickness of the color-changing layer. If the content of organic dye is too high or if the content of organic dye is too low, it may be difficult to confirm a change in color before and after color change by visual observation.

In the present invention, colorants and pigments other than the organic dyes mentioned above may also be present. For example, a colorant and the like that do not change color or are unlikely to change color in a plasma treatment atmosphere may be added. Examples of colorants and the like that do not change color or are unlikely to change color include organic pigments, titanium oxide, and the like. This can enhance color tone change when the organic dye changes color, and can further enhance the visual color change recognition effect. Colorants and the like that are unlikely to change color in a plasma treatment atmosphere may include those that slightly change color due to physical etching action in a plasma treatment atmosphere.

Photopolymerization Initiator, Silica, and Hydrophobic Alumina

The ink composition of the present invention contains at least one member selected from the group consisting of photopolymerization initiators, silica, and hydrophobic alumina, as a color change accelerator that improves the color change rate of an organic dye in a plasma treatment atmosphere. Hydrophobic alumina as used here means alumina surface-treated with a hydrophobic group-containing compound. Examples of hydrophobic groups include dimethylsilyl groups, trimethylsilyl groups, dimethylpolysiloxane groups, dimethylsiloxane groups, aminoalkylsilyl groups, alkylsilyl groups, methacrylsilyl groups, and the like. Using such a color change accelerator in combination with an organic dye can provide excellent detection sensitivity and makes it possible to control the color change rate by adjusting the content of the color change accelerator.

Although the detailed reason why photopolymerization initiators, silica, and hydrophobic alumina act as color change accelerators is unknown, photopolymerization initiators and hydrophobic alumina are considered to generate radicals in a plasma treatment atmosphere to change the structures of organic dyes (such as partial decomposition or bond cleavage), thereby exhibiting a color-change-accelerating effect. Silica is considered to exhibit a color-change-accelerating effect because the surface area to which organic dyes adhere increases due to the porous surface of silica and silica makes the surface of the coating film (color-changing layer) itself of the ink composition of the present invention porous to thereby provide the effect of creating an environment in which plasma is easily struck.

Any photopolymerization initiator can be used without limitation. For example, preferable is at least one member selected from the group consisting of alkylphenone-based photopolymerization initiators, acylphosphine oxide-based photopolymerization initiators, titanocene-based photopolymerization initiators, acetophenone-based photopolymerization initiators, benzophenone-based photopolymerization initiators, thioxanthone-based photopolymerization initiators, cationic photopolymerization initiators, and anionic photopolymerization initiators. More preferred among these photopolymerization initiators is at least one member selected from the group consisting of alkylphenone-based photopolymerization initiators and acylphosphine oxide-based photopolymerization initiators.

The content of the photopolymerization initiator can be appropriately determined according to, for example, the types of photopolymerization initiator and organic dye used. In consideration of the preservability in the ink composition and color-change-accelerating effect, the content of the photopolymerization initiator in the ink composition is generally preferably about 0.05 to 20 wt. %, and particularly preferably 1 to 10 wt. %, when the content of the photopolymerization initiator exceeds 20 wt. %, the photopolymerization initiator may not be dissolved completely in the ink composition. When the content of the photopolymerization initiator is less than 0.05 wt. % the color-change-accelerating effect may not be exhibited sufficiently.

Any silica can be used without limitation, and for example, hydrophobic silica is preferable. Silica surface-treated to impart hydrophobicity may be used. The average particle size of silica is not limited and is preferably 5 to 100 nm, and more preferably 5 to 50 nm.

The content of the silica can be appropriately determined according to, for example, the types of silica and organic dye used. In consideration of the preservability in the composition and color-change-accelerating effect, the content of the silica in the ink composition is generally preferably about 1 to 30 wt. %, and particularly preferably 2 to 20 wt. %. When the content of the silica exceeds 20 wt. %, the color-change-accelerating effect may not be exhibited sufficiently. When the content of the silica is less than 0.1 wt. %, the color-change-accelerating effect may not be exhibited sufficiently.

The hydrophobic alumina may be any alumina surface-treated with a hydrophobic group-containing compound. Untreated alumina and hydrophilic alumina can be used as extenders as described below, but are clearly distinguished from the hydrophobic alumina by the presence or absence of surface treatment and a difference in the type of surface treatment. The average particle size of the hydrophobic alumina is not limited and is preferably 5 to 100 nm, and more preferably 5 to 50 nm.

The content of the hydrophobic alumina can be appropriately determined according to, for example, the degree of hydrophobicity and the type of organic dye used. In consideration of the preservability in the composition and color-change-accelerating effect, the content of the hydrophobic alumina in ink composition is generally preferably about 0.5 to 50 wt. %, and particularly preferably 1 to 30 wt. %. When the content of the hydrophobic alumina exceeds 50 wt. %, the fixing properties of the coating film of the ink composition may decrease. When the content of the hydrophobic alumina is less than 0.5 wt. %, the color-change-accelerating effect may not be exhibited sufficiently.

Extender

Any extender can be used without particular limitation, and examples of extenders include bentonite, activated clay, untreated alumina, hydrophilic alumina, silica gel, and like inorganic materials. Materials known as extender pigments can also be used. Of these, at least one member selected from the group consisting of silica gel and hydrophilic alumina is preferable. The extenders can be used singly or in a combination of two or more. When an extender is used, the extender makes the surface of the coating film (color-changing layer) itself of the ink composition of the present invention porous to thereby provide the effect of creating an environment in which plasma is easily struck. Thus, the color-change-accelerating effect based on the addition of the extender can be obtained in addition to the color-change-accelerating effect of the present invention based on the photopolymerization initiator, silica, and hydrophobic alumina.

The content of the extender can be appropriately determined according to, for example, the types of extender and coloring agent used. The content of the extender in the ink composition is generally preferably about 1 to 30 wt. %, and particularly preferably 2 to 20 wt. %.

Binder Resin

The binder resin may be appropriately selected according to, for example, the type of base material in the plasma treatment detection indicator described below. For example, known resin components used in ink compositions for writing, printing, etc., can be used. Examples of binder resins include maleic resins, ketone resins, polyvinyl butyral resins, cellulose resins, acrylic resins, styrene maleic resins, styrene acrylic acid resins, polyester resins, polyamide resins, polyacrylonitrile resins, polyimide resins, polyvinyl pyrrolidone resins, polyacrylamide resins, polyvinyl imidazole resins, polyethylene imine resins, amino resins, and the like.

In the present invention, cellulose resins can be particularly suitably used. The use of a cellulose resin can impart excellent fixing properties even when the ink composition contains silica, hydrophobic alumina, an extender, or the like. Thus, after the coating film of the ink composition is formed on a base material, the coating film can be efficiently prevented from, for example, falling and detaching from the base material. In addition, effectively producing cracks on the surface of the coating film of the ink composition is considered to attain a color-change-accelerating effect because it has the effect of creating an environment in which plasma is easily struck.

Further, in the present invention, polyvinyl butyral resins can be suitably used. The use of a polyvinyl butyral resin can improve the light resistance of the ink composition of the present invention, which contains an organic dye, and the coating film (color-changing layer described below) of the composition, compared with the case where other binder resins (in particular, cellulose resins) are used or the case where no binder resin is used. More specifically, when the ink composition and the coating film of the ink composition are irradiated with light including ultraviolet rays, such as a fluorescent light, even though it is not plasma treatment, a slight color change may be observed. The use of a polyvinyl butyral resin as a binder resin can suppress color changes of the ink composition and the coating film (color-changing layer) of the composition caused when they are irradiated with light including ultraviolet rays, thereby improving their light resistance.

In the present invention, the binder resins may be all or partially nitrogen-containing polymers other than the resins mentioned above. The nitrogen-containing polymers function as sensitivity enhancers as well as binders. Specifically, the use of such a sensitivity enhancer can further enhance the accuracy (sensitivity) of plasma treatment detection. Because this ensures color change even in a package for detecting plasma treatment, the indicator can be used very advantageously for the package.

Examples of suitably usable nitrogen-containing polymers include synthetic resins, such as polyamide resins, polyimide resins, polyacrylonitrile resins, amino resins, polyacrylamides, polyvinylpyrrolidones, polyvinylimidazoles, polyethyleneimines, and the like. These resins can be used singly or in a combination of two or more. In particular, polyamide resins are preferably used in the present invention. The type, molecular weight, etc., of polyamide resin are not particularly limited, and known or commercially available polyamide resins can be used. Among these, a polyamide resin that is a reaction product of a dimer of linoleic acid with a diamine or polyamine (a long-chain linear polymer) is suitable for use. Polyamide resins are thermoplastic resins with a molecular weight of 4000 to 7000. Commercially available products of these resins can also be used.

In the present invention, using phenolic resin(s) other than the resins mentioned above as at least one or all of the binder resins can enhance heat resistance of the ink composition and the coating film (color-changing layer) of the ink composition.

The phenolic resin may be any resin that has a phenol structure. For example, at least one member selected from the group consisting of alkylphenol resins, terpene phenolic resins, and rosin-modified phenolic resins can be suitably used. Such phenolic resins can be used singly or in a combination of two or more.

The content of the binder resin can be appropriately determined according to, for example, the types of binder resin and organic dye used. The content of the binder resin in the ink composition is generally preferably about 50 wt. % or less, and particularly preferably 5 to 35 wt. %. When a nitrogen-containing polymer is used as a binder resin, the content of the nitrogen-containing polymer in the ink composition is preferably about 0.1 to 50 wt. %, and particularly preferably 1 to 20 wt. %. The content of the binder resin has an influence on the color change rate of the color-changing layer. A high content of the binder resin tends to decrease the color change rate of the color-changing layer, whereas a low content of the binder resin tends to increase the color change rate of the color-changing layer. Thus, to increase the color change rate, the ink composition containing no binder resin can also be used. When the ink composition contains no binder resin or the amount of the binder resin in the ink composition is small, the fixing properties of the ink composition are likely to decrease; however, in such a case, using a base material with high fixing properties as described below can be considered.

Other Additives

If required, the ink composition may appropriately contain components used in known inks, such as solvents, leveling agents, antifoaming agents, UV absorbers, and surface conditioners.

Solvents that can be used in the present invention may be any solvent that is typically used in ink compositions for printing writing, etc. Usable solvents are various solvents such as alcohol-based, polyhydric alcohol-based, ester-based, ether-based, ketone-based, hydrocarbon-based, and glycol ether-based solvents. The solvent to be used may be appropriately selected according to the solubility of the organic dye and binder resin used, etc. The solvents can be used singly or in a combination of two or more.

The content of the solvent can be appropriately determined according to, for example, the types of solvent and organic dye used. The content of the solvent in the ink composition is generally preferably about 40 to 95 wt. %, and particularly preferably 60 to 90 wt. %.

The components of the ink composition of the present invention can be added all at once or sequentially, and mixed uniformly using a known stirrer, such as a homogenizer or a dissolver. For example, the organic dye described above and at least one member selected from the group consisting of color change accelerators and binder resins (other additives as required, except for extenders) may be sequentially added to a solvent; finally, an extender may be added as required; and the resultant mixture may be mixed and stirred using a stirrer.

2. Plasma Treatment Detection Indicator

The indicator of the present invention comprises a color-changing layer formed from the ink composition of the present invention. The color-changing layer can typically be formed by applying or printing the ink composition of the present invention on a base material. Any base material can be used as the base material insofar as the color-changing layer can be formed on the base material.

Examples of base materials include metals or alloys, ceramics, glass, concrete, plastics (polyethylene terephthalate (PET), polypropylene, nylon, polystyrene, polysulfone, polycarbonate, polyimide, etc.), fibers (non-woven fabric, woven fabric, paper, other fibrous sheets), and composite materials thereof. Synthetic resin fiber paper (synthetic paper), such as polypropylene synthetic paper and polyethylene synthetic paper, can also be suitably used. When the ink composition of the present invention contains no resin binder or the content of the resin binder is small, permeable base materials, such as fibers that can be impregnated with the ink composition, among these base materials can be suitably used from the viewpoint of the fixing properties of the ink composition.

Embodiments of the color change of the color-changing layer in the present invention include those in which the color changes from colorless to colored and those in which the color changes from one color to another.

The color-changing layer can be formed using the ink composition of the present invention according to a known printing method, such as silk-screen printing, gravure printing, offset printing, relief printing, or flexographic printing. The color-changing layer can also be formed by various methods other than printing methods. For example, the color-changing layer can be formed by immersing a base material into an ink composition.

The color-changing layer preferably has cracks on the surface. Specifically, the color-changing layer is preferably porous with open pores formed on the surface of the layer. This structure can further enhance the sensitivity in plasma treatment detection. In this case, the desired color change effect can be obtained even when the color-changing layer is disposed in the plasma treatment detection package. Cracks can be effectively formed especially by using a cellulose resin as a binder resin for the ink composition of the present invention. Specifically, the use of a cellulose resin enables the formation of cracks as described above, while maintaining good fixing properties.

In the present invention, to further enhance the visual recognition effect when the color-changing layer changes color, for example, a non-color-changing layer may be formed between the base material and the color-changing layer. The non-color-changing layer can typically be formed by using a commercially available normal color ink. For example, water-based inks, oil-based inks, solventless inks, and the like can be used. The ink for use in the formation of the non-color-changing layer may contain components used in known inks, such as resin binders, extenders, and solvents.

The non-color-changing layer may be formed in the same manner as in the formation of the color-changing layer. For example, the non-color-changing layer can be formed by using a normal color ink according to a known printing method, such as silk-screen printing, gravure printing, offset printing, relief printing, or flexographic printing.

The indicator of the present invention is applicable to any plasma treatment using a gas for generating plasma. Thus, the indicator can be used for both reduced-pressure plasma treatment and atmospheric-pressure plasma treatment.

Reduced-pressure plasma treatments can be used, for example, in film production, ashing, cleaning, surface modification, etc., of flat-panel displays (e.g., liquid crystal displays); film production, ashing, cleaning, surface modification, etc., in semiconductor manufacturing processes; cleaning, surface modification, etc., of mounting substrates or printed-circuit substrates; sterilization, etc., of medical instruments; and cleaning, surface modification, etc., of mounted components.

Atmospheric-pressure plasma treatments can be used, for example, in cleaning, surface modification, etc., of flat-panel displays (e.g., liquid crystal displays); cleaning, surface modification, etc., of mounting substrates or printed-circuit substrates; surface modification of automobiles, aircraft components, etc.; and disinfection, sterilization, medical treatment, etc., in the medical field (dentistry or surgery).

The gas for generating reduced-pressure plasma may be any gas that can generate plasma by applying AC voltage, pulse voltage, high-frequency waves, microwaves, etc., under reduced pressure. Examples of such gases include oxygen, nitrogen, hydrogen, chlorine, hydrogen peroxide, helium, argon, silane, ammonia, sulfur bromide, water vapor, nitrous oxide, tetraethoxysilane, carbon tetrachloride, trifluoromethane, carbon tetrachloride, silicon tetrachloride, sulfur hexafluoride, titanium tetrachloride, dichlorosilane, trimethylgallium, trimethylindium, trimethylaluminum, and the like. These gases for generating reduced-pressure plasma can be used singly or in a combination of two or more.

The gas for generating atmospheric-pressure plasma may be any gas that can generate plasma by applying AC voltage, pulse voltage, high-frequency waves, microwaves, etc., under atmospheric pressure. Examples of such gases include oxygen, nitrogen, hydrogen, argon, helium, air, and the like. These gases for generating atmospheric-pressure plasma can be used singly or in a combination of two or more.

When the indicator of the present invention is used, for example, the indicator of the present invention may be placed in a plasma treatment device that uses a gas for generating plasma (specifically a device for plasma treatment that generates plasma by application of AC voltage, pulse voltage, high-frequency waves, microwaves, etc., in an atmosphere containing a gas for generating plasma to perform plasma treatment) or placed on or near the article(s) to be treated that are accommodated in the device, and may be exposed to a plasma treatment atmosphere. In this case, it can be detected from the color change of the indicator placed in the device that a predetermined plasma treatment has been performed.

The indicator of the present invention can be used in the form of an indicator card as is. If the color-changing layer is in the form of a known bar code and the bar code has its conditions set so that it can be read by a bar code reader at the stage where a predetermined plasma treatment has been completed (degree of color change), completion of plasma treatment and subsequent plasma-treated article distribution management can be centrally managed with the bar code. The present invention also includes inventions of an indicator, a method for plasma treatment management, and a method for distribution management used for this purpose.

3. Package

The present invention includes a package for plasma treatment comprising a gas-permeable package and the indicator of the present invention placed in the package.

The gas-permeable package is preferably a package that can be subjected to a plasma treatment with article(s) to be treated being contained in the package. Known or commercially available packages that are used as packages (pouches) for plasma treatment can be used. For example, a package formed of polyethylene fiber (polyethylene synthetic paper) can be suitably used. More specifically, after the article(s) to be treated are placed in the package in which the indicator of the present invention is placed, and the opening is sealed by heat-sealing or the like, the entire package can be treated in the plasma treatment device.

The indicator of the present invention is placed in the package. The method for disposing the indicator is not limited. In addition to methods using adhesives, heat-sealing, etc., the indicator can also be formed by directly applying or printing the ink composition of the present invention onto the inner surface of the package. When an indicator is formed by such application or printing, the indicator can also be formed at the stage of manufacturing the package.

The package of the present invention preferably has a transparent window in a part of the package so as to allow the indicator to be visually checked from the outside. For example, the package may be formed using a transparent sheet and the polyethylene synthetic paper mentioned above, and the indicator may be placed on the inner surface of the package at such a position as to allow the indicator to be visually checked through the transparent sheet.

When plasma treatment is performed using the package of the present invention, for example, a method including the following steps may be used: a step of placing article(s) to be treated into the package, a step of sealing the package containing the article(s) to be treated, and a step of disposing the package in a plasma treatment atmosphere. More specifically, after the article(s) to be treated are placed in the package, the package is sealed according to a known method, such as heat sealing. Subsequently, the entire package is placed in a plasma treatment atmosphere. For example, the package is placed in a treatment chamber of a known or commercially available plasma treatment device, and subjected to the treatment. After the treatment has been completed, the entire package is removed from the treatment chamber, and the treated article(s) can be kept in the package as is until use. In this plasma treatment, the package is preferably kept in a plasma treatment atmosphere until the color of the color-changing layer of the indicator changes.

EXAMPLES

The following describes Examples and Comparative Examples to further clarify the features of the present invention. However, the present invention is not limited to the embodiments of the Examples.

Examples 1 to 13 and Comparative Examples 1 to 7

Ink compositions were prepared by mixing the components according to the formulations shown in Table 1.

The ink compositions were individually silk-screen-printed on a base material (printing paper produced by Lintec Corporation, trade name Nuage), and force-dried in a thermostatic chamber (75° C.) for 15 minutes to form color-changing layers, thereby obtaining indicators.

Each indicator was subjected to a color change test.

The test methods and evaluation criteria are as follows.

Color Change Test 1: Reduced-Pressure Plasma Treatment

First, the chromaticity $L^*a^*b^*$ of the color-changing layer of each indicator (before plasma treatment) was measured with an NR-11A handheld colorimeter produced by Nippon Denshoku Industries Co., Ltd.

Next, each indicator was placed in a BP-1 parallel-plate high-frequency plasma treatment device (produced by Samco Inc.).

$O_2$ gas and Ar gas were prepared as gases for generating plasma, and plasma treatment was performed under the following conditions. The chromaticity $L^*a^*b^*$ of each color-changing layer after the plasma treatment was measured in the same manner as above.

The chromaticity before the plasma treatment was defined as $L^*_1$, $a^*_1$, and $b^*_1$, whereas the chromaticity after the plasma treatment was defined as $L^*_2$, $a^*_2$, and $b^*_2$. The difference in chromaticity (color difference) between the two, which is indicated by $\Delta E^*ab$, was calculated using the following equation. Table 1 shows the color difference of the color-changing layer in each indicator.

$$\text{Color difference } \Delta E^*ab = [(L^*_2 - L^*_1)^2 + (a^*_2 - a^*_1)^2 + (b^*_2 - b^*_1)^2]^{1/2}$$

Plasma Treatment Conditions

Treatment Conditions Using $O_2$ Gas $O_2$ gas: 10 ml/min

Electric power: 15 W, pressure: 100 Pa, distance between electrodes: 50 mm

Treatment Time: 10 min

Treatment Conditions Using Ar Gas
    Ar gas: 20 ml/min
    Electric power: 75 W, pressure: 20 Pa, distance between electrodes: 50 mm
    Treatment Time: 10 min Color Change Test 2: Atmospheric-Pressure Plasma Treatment First, the chromaticity L*a*b* of the color-changing layer of each indicator (before plasma treatment) was measured with an NR-11A handheld colorimeter produced by Nippon Denshoku Industries Co., Ltd.

Next, each indicator was placed in a Tough Plasma atmospheric-pressure plasma treatment device (produced by Fuji Machine Mfg. Co., Ltd.).

The chromaticity before the plasma treatment was defined as $L^*_1$, $a^*_1$, and $b^*_1$, whereas the chromaticity after the plasma treatment was defined as $L^*_2$, $a^*_2$, and $b^*_2$. The difference in chromaticity (color difference) between the two, which is indicated by $\Delta E^*ab$, was calculated using the following equation. Table 1 shows the color difference of the color-changing layer in each indicator.

$$\text{Color difference } \Delta E^*ab = [(L^*_2 - L^*_1)^2 + (a^*_2 - a^*_1)^2 + (b^*_2 - b^*_1)^2]^{1/2}$$

Plasma Treatment Conditions
    Gas: $N_2$: 29.7 L/min dry air: 0.3 L/min,
    Irradiation distance: 10 mm,
    Treatment Time: 25 mm/sec×one time Discussion 1

In each of the plasma treatment detection indicators of the Examples, which use an organic dye as a color-changing component in a plasma treatment atmosphere and further contain at least one member selected from the group consisting of photopolymerization initiators, silica, and hydrophobic alumina, the color difference ($\Delta E^*ab$) was 5 or more in all the plasma treatments, and the completion of the plasma treatments was visually determined reliably. In contrast, some of the plasma treatment detection indicators of the Comparative Examples exhibited almost no color change depending on treatment conditions, and, in particular, it was found that the plasma treatment detection indicators of the Comparative Examples were inferior to those of the Examples in the color change in the Tough Plasma (atmospheric-pressure plasma).

Light Resistance Test

Each indicator was subjected to a light resistance test.

First, the chromaticity L*a*b* of the color-changing layer of each indicator (before plasma treatment and before white light irradiation) was measured with an NR-11A handheld colorimeter produced by Nippon Denshoku Industries Co., Ltd.

Next, the color-changing layer of each indicator was irradiated using a fluorescent lamp produced by Sharp Corporation (25 watts, white light) from a distance of 50 cm. Thereafter, the chromaticity L*a*b* of each color-changing layer (before plasma treatment and after white light irradiation) was measured in the same manner as above.

The chromaticity before the white light irradiation was defined as $L^*_1$, $a^*_1$, and $b^*_1$, whereas the chromaticity after the white light irradiation was defined as $L^*_2$, $a^*_2$, and $b^*_2$. The difference in chromaticity (color difference) between the two, which is indicated by $\Delta E^*ab$, was calculated using the following equation. Table 1 shows the color difference of the color-changing layer in each indicator.

$$\text{Color difference } \Delta E^*ab = [(L^*_2 - L^*_1)^2 + (a^*_2 - a^*_1)^2 + (b^*_2 - b^*_1)^2]^{1/2}$$

Discussion 2

The results showed that if a resin other than a polyvinyl butyral resin is used or no binder resin is used as shown in Examples 1 to 8, 12, and 13 among Examples 1 to 13, slight color change is observed when the color-changing layer is irradiated with white light, whereas the use of a polyvinyl butyral resin as a binder resin makes it possible to suppress color change of the color-changing layer caused when irradiated with white light without impairing color change due to plasma treatment and improve light resistance, as shown in Examples 9 to 11.

TABLE 1

| | Formulation | Ex 1 | Ex 2 | Ex 3 | Ex 4 | Ex 5 | Ex 6 | Ex 7 | Ex 8 | Ex 9 | Ex 10 | Ex 11 | Ex 12 | Ex 13 | Comp 1 | Comp 2 | Comp 3 | Comp 4 | Comp 5 | Comp 6 | Comp 7 |
|---|---|---|---|---|---|---|---|---|---|---|---|---|---|---|---|---|---|---|---|---|---|
| Dye | Basic Blue 7 (triarylmethane dye) | 0.2 | | | | | | | | | | | 0.2 | 0.2 | 0.2 | | | | | | |
| | Solvent Blue 58 (anthraquinone dye) | | 0.2 | | | | 0.2 | | | | 0.2 | | | | | 0.2 | | | | 0.2 | |
| | Solvent Blue 5 (triarylmethane dye) | | | 0.2 | | | | 0.2 | | | | | | | | | 0.2 | | | | |
| | Direct Blue 86 (phthalocyanine dye) | | | | 0.2 | | | | 0.2 | | | | | | | | | 0.2 | | | |
| | Disperse Violet 1 (anthraquinone dye) | | | | | 0.2 | | | | 0.2 | | 0.2 | | | | | | | 0.2 | | 0.2 |
| Pigment | C.I. Pigment Yellow 3 (disazo pigment) | | | | | | | | | | | | | | | | | | | | |
| | C.I. Pigment Green 7 (phthalocyanine pigment) | 6.0 | | 8.0 | | | | 6.0 | 8.0 | | | | 6.0 | | | | 8.0 | | | | 6.0 |
| Photopolymerization initiator | 2-hydroxy-1-{4-[4-(2-hydroxy-2-methyl-propionyl)-benzyl]-phenyl}-2-methyl-propan-1-one (produced by Ciba Japan) | | | | | | | | | 7.0 | | | | | | | | 7.0 | 6.0 | | |
| | 2,4,6-trimethylbenzoyl-diphenyl-phosphine oxide (produced by Ciba Japan) | | | | 7.0 | | | | | | 10.0 | | | | | | | | | | |
| | Mixture of oxy-phenyl-acetic acid 2-[2-oxo-2-phenyl-acetoxy-ethoxy]-ethyl ester and 2-[2-hydroxy-ethoxy]-ethyl ester (produced by BASF) | | 10.0 | | | 5.0 | 10.0 | 10.0 | 5.0 | | | 5.0 | | | | | | | | | |
| | bis(η5-2,4-cyclopentadien-1-yl)-bis(2,6-difluoro-3-(1H-pyrrol-1-yl)-phenyl)-titanium (produced by Ciba Japan) | | | | | 5.0 | | | | | | 5.0 | | | | | | | | | 6.0 |
| Alumina | AEROXIDE AluC805 (hydrophobic alumina, produced by Nippon Aerosil Co., Ltd.) | 10.0 | | | | | | | | | | | | 10.0 | | | | | | | |
| | AEROXIDE AluC (hydrophilic alumina, extender, produced by Nippon Aerosil Co., Ltd.) | | | | | | | | | | | 12.0 | 10.0 | | | | | | | | |
| Silica | Aerosil R-972 (silica produced by Nippon Aerosil Co., Ltd.) | | 12.0 | 10.0 | | 12.0 | 10.0 | | | | 12.0 | | | | | | | 10.0 | | 10.0 | |
| Resin | Nitrocellulose RS7 (nitrocellulose produced by SNPE Japan) | | 10.0 | | | | | | | | | | | | 8.0 | 8.0 | | | | | |
| | Tamanol 100S (alkylphenol produced by Arakawa Chemical Industries, Ltd.) | | | | | 8.0 | | | | | | | | | | | 8.0 | | | | |
| | MOWITAL PVB B-30H (kuraray, polyvinyl butyral) | | | | | | | | | 10.0 | 10.0 | 8.0 | | | | | | | 6.0 | | |
| | Versamid JP802 (polyamide produced by BASF) | | | | 10.0 | | | | | | | | | | | | | | | | |
| Solvent | Propylene glycol monomethyl ether | | 7.8 | 8.8 | 9.8 | 9.8 | 10.0 | 10.0 | 8.8 | 9.8 | 7.8 | 9.8 | 10.0 | 10.0 | 10.0 | 10.0 | 10.0 | 10.0 | 10.0 | 10.0 | 10.0 |
| | Butyl cellosolve | 83.8 | 60.0 | 73.0 | 73.0 | 60.0 | 79.8 | 73.8 | 73.0 | 73.0 | 60.0 | 60.0 | 73.8 | 79.8 | 81.8 | 89.8 | 81.8 | 72.8 | 75.8 | 79.8 | 73.8 |
| | Total | 100.0 | 100.0 | 100.0 | 100.0 | 100.0 | 100.0 | 100.0 | 100.0 | 100.0 | 100.0 | 100.0 | 100.0 | 100.0 | 100.0 | 108.0 | 100.0 | 100.0 | 100.0 | 100.0 | 100.0 |
| Color change test | Parallel plate O₂ plasma gas ΔE*ab between before and after treatment | 10 | 24 | 20 | 16 | 22 | 16 | 20 | 22 | 16 | 25 | 22 | 14 | 12 | 0 | 0 | 2 | 3 | 1 | 2 | 2 |
| | Parallel plate Ar plasma gas ΔE*ab between before and after treatment | 7 | 26 | 16 | 9 | 21 | 15 | 22 | 16 | 9 | 26 | 22 | 12 | 8 | 0 | 0 | 2 | 2 | 1 | 1 | 3 |
| | Tough Plasma N₂ gas + air ΔE*ab between before and after treatment | 13 | 24 | 14 | 10 | 21 | 18 | 21 | 18 | 10 | 24 | 22 | 14 | 13 | 1 | 1 | 3 | 4 | 3 | 2 | 3 |
| | Light resistance | 7 | 9 | 6 | 7 | 8 | 5 | 8 | 7 | 2 | 2 | 3 | 8 | 7 | 8 | 1 | 1 | 1 | 1 | 1 | 1 |

The invention claimed is:

1. An ink composition for detecting plasma treatment, the composition comprising an organic dye, a photopolymerization initiator, and at least one member selected from the group consisting of silica and hydrophobic alumina,
    wherein the organic dye is at least one member selected from the group consisting of nitroso dyes, nitro dyes, monoazo dyes, diazo dyes, triazo dyes, polyazo dyes, azoic dyes, stilbene dyes, carotenoid dyes, diarylmethane dyes, triarylmethane dyes, acridine dyes, quinoline dyes, methine dyes, thiazole dyes, indamine dyes, indophenol dyes, azine dyes, oxazine dyes, thiazine dyes, sulfur dyes, lactone dyes, hydroxyketone dyes, aminoketone dyes, anthraquinone dyes, indigoid dyes, phthalocyanine dyes, natural dyes, and oxidation dyes.

2. The ink composition according to claim 1, further comprising a cellulose resin.

3. The ink composition according to claim 1, further comprising a polyvinyl butyral resin.

4. The ink composition according to claim 1, wherein the photopolymerization initiator is at least one member selected from the group consisting of alkylphenone-based photopolymerization initiators, acylphosphine oxide-based photopolymerization initiators, titanocene-based photopolymerization initiators, acetophenone-based photopolymerization initiators, benzophenone-based photopolymerization initiators, thioxanthone-based photopolymerization initiators, cationic photopolymerization initiators, and anionic photopolymerization initiators.

5. The ink composition according to claim 1, further comprising an extender.

6. A plasma treatment detection indicator comprising a color-changing layer formed from the ink composition according to claim 1.

7. A plasma treatment package comprising a gas-permeable package and the indicator according to claim 6 in the gas-permeable package.

8. The package according to claim 7, having a transparent window in a part of the package so as to enable the indicator to be checked from the outside.

9. A plasma treatment method comprising placing an article to be treated in the package according to claim 7, sealing the package containing the article to be treated, and placing the package in a plasma treatment atmosphere.

10. The treatment method according to claim 9, wherein the package is placed in the plasma treatment atmosphere until the color-changing layer of the indicator changes color.

* * * * *